United States Patent [19]

Buck

[11] 4,360,514

[45] Nov. 23, 1982

[54] SULFONATED ALKYLNAPHTHALENES AS DENTAL PLAQUE BARRIERS

[75] Inventor: Carl J. Buck, Berkeley Heights, N.J.

[73] Assignee: Johnson & Johnson Products Inc., New Brunswick, N.J.

[21] Appl. No.: 172,488

[22] Filed: Jul. 25, 1980

[51] Int. Cl.³ .................. A61K 7/16; A61K 7/22; A61K 31/315; A61K 31/185

[52] U.S. Cl. .................................. 424/56; 424/54; 424/289; 424/315; 424/316

[58] Field of Search .................. 424/48–56, 424/78, 289, 315, 316, 505 C; 260/512 R, 505 R

[56] References Cited

U.S. PATENT DOCUMENTS

| | | | |
|---|---|---|---|
| 2,215,457 | 9/1940 | Anderson | 424/56 |
| 3,282,779 | 11/1966 | Pensack et al. | 424/315 |
| 3,812,178 | 5/1974 | Weedon | 260/512 |
| 3,836,484 | 9/1974 | Danzik et al. | 260/505 R |
| 4,150,112 | 4/1979 | Wagenknecht et al. | 424/48 |

FOREIGN PATENT DOCUMENTS

| | | | |
|---|---|---|---|
| 47-38967 | 2/1972 | Japan | 424/315 |
| 322193 | 11/1929 | United Kingdom | 424/315 |
| 1296952 | 11/1972 | United Kingdom . | |
| 1507772 | 4/1978 | United Kingdom . | |

*Primary Examiner*—Douglas W. Robinson

[57] ABSTRACT

Compositions and methods for preventing the attachment of dental plaque to the surfaces of the teeth of mammals comprise certain pharmaceutically acceptable salts of sulfonated alkylnaphthalenes. They are used in pharmaceutically acceptable vehicles that are periodically applied to teeth.

3 Claims, No Drawings

SULFONATED ALKYLNAPHTHALENES AS DENTAL PLAQUE BARRIERS

TECHNICAL FIELD

This invention relates to oral hygiene compositions and to methods using such compositions to prevent attachment of bacteria to teeth. More particularly it relates to certain sulfonated alkylnaphthalenes that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, by fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

Hydrophilic sulfonic acid salt derivatives of certain monoalkylnaphthalenes and dialkylnaphthalenes have been synthesized and found to inhibit the deposition of dental plaque onto human teeth. These alkylnaphthalene sulfonates are substantially soluble in water or water/organic solvent vehicles and are applied to teeth from various dentifrice formulations, mouth rinses, or other oral hygiene procedures. While the mechanism of action of these sulfonated derivatives in retarding plaque deposition is not known with absolute certainty, it is presumed that films of the anionically charged compounds are deposited on teeth. A mutual repulsion effect is thought to arise between the negatively charged microorganisms responsible for plaque generation and the negatively charged films of alkylnaphthalene sulfonates. The alkylnaphthalene sulfonates of this invention are especially effective as components of dentifrices and other oral hygiene preparations in reducing dental plaque deposition on teeth.

A particular feature of the monoalkylnaphthalene and dialkylnaphthalene sulfonate salts of this invention, which appears to govern their effectiveness as agents for the reduction of plaque deposition, is the balance between the hydrophobic and hydrophilic properties of these compounds. The hydrophobic groups in the alkylnaphthalene sulfonates are the naphthalene ring and the substituent alkyl groups. The sulfonate group is the hydrophilic moiety. Accordingly, it has been found expedient to adjust the hydrophobic/hydrophilic balance in the alkylnaphthalene sulfonates of this invention by independently varying both the size of the hydrophobic alkyl group and the number of sulfonate groups.

The sulfonated derivatives which are useful for dental plaque control in accordance with the present invention are monoalkylnaphthalene monosulfonate salts of structure (A),

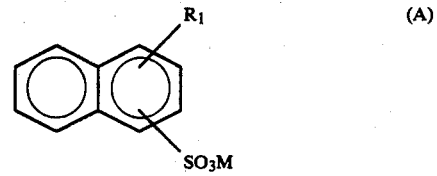

dialkylnaphthalene monosulfonate salts of structure (B),

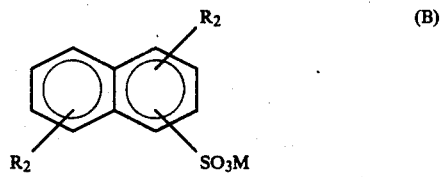

monoalkylnaphthalene disulfonate salts of structure (C),

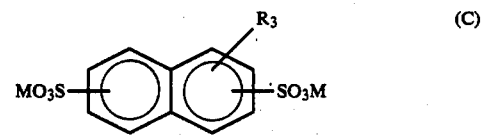

and dialkylnaphthalene disulfonate salts of structure (D),

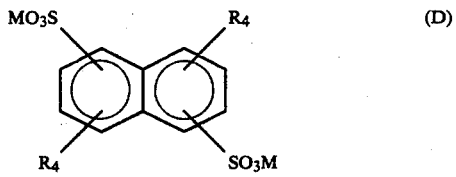

wherein $R_1$ is a linear or branched alkyl having 4 to 20 carbon atoms, $R_2$ is a linear or branched alkyl having 4 to 12 carbon atoms, $R_3$ is a linear or branched alkyl having 16 to 20 carbon atoms, $R_4$ is a linear or branched alkyl having 8 to 20 carbon atoms, and M is selected from the group consisting of lithium, sodium, potassium, calcium, magnesium, zinc, aluminum, ammonium and the substituted ammonium ions derived from pharmaceutically acceptable organic amines.

Certain of the alkylnaphthalene sulfonates useful in the practice of this invention are items of commerce. These include the following sulfonic acids and salts sold by King Industries, Inc., Norwalk, Connecticut: (a) Dinonylnaphthalene sulfonic acid, available as "Synex TM Liquid Ion Exchange Reagents"—"DN-040" "DN-051", and "DN-052"; (b) Sodium dinonylnaphthalene sulfonate, as "Synex TM DN-150"; (c) Dinonylnaphthalene disulfonic acid, as "Nacure TM 155:DMEA Salt"; (d) Sodium dinonylnaphthalene disulfonate; (e) Didodecylnaphthalene sulfonic acid, as "Synex TM DD-040" and "DD-052".

The alkylnaphthalene sulfonates of this invention (structures (A) through (D)) can be synthesized by a three-step process consisting of (1) Friedel-Crafts alkylation of naphthalene to afford either the mono- or dialkylnaphthalene, (2) Aromatic sulfonation to either the mono- or disulfonic acid derivative, and (3) Conversion of the sulfonic acid group to the metal, ammonium, or substituted ammonium salt. The general sequence for preparation of the sulfonic acid intermediates is shown schematically in equation (1)

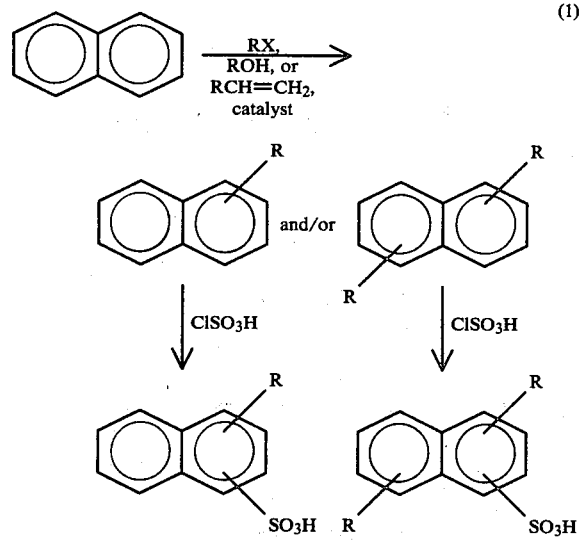

The Friedel-Crafts method for the alkylation of naphthalene with alkyl halides, alcohols, or olefins to the corresponding alkylnaphthalenes has been extensively described in the literature and reviewed e.g. by C. C. Price in "Organic Reactions", Volume 3, Chapter 1, pages 1–82, John Wiley & Sons, Inc., 1946. The alkylation reaction, catalyzed by materials such as aluminum chloride, antimony pentachloride, ferric chloride, stannic chloride, zinc chloride, hydrogen fluoride, sulfuric acid, and phosphoric acid, must be carefully controlled to achieve the degree of alkylation required and minimize formation of undesired polyalkylation and rearrangement products (C. C. Price, supra). Rearrangement of the alkyl group introduced by the Friedel-Crafts alkylation reaction is a common occurrence, so that alkylations with linear alkyl halides, alcohols, and olefins often result in the formation of a mixture of linear and branched alkyl-substituted aromatic compounds. The position of substitution of the alkyl groups on the aromatic ring is dependent on the reaction conditions and type of catalyst utilized.

The commonly available monoalkylnaphthalene and dialkylnaphthalene compounds that are useful as intermediates for the preparation of the sulfonated derivatives of this invention consist largely of mixed linear and branched alkylated naphthalenes, wherein the distribution of the alkyl groups on the aromatic ring is generally random.

Naphthalene substituted with linear alkyl groups can be synthesized in two steps: (1) Friedel-Crafts acylation of naphthalene with an acyl chloride, RCOCl (where R is a linear alkyl group), to an acylated naphthalene, followed by (2) Clemmenson reduction or Wolff-Kishner reduction of the carbonyl group. These reactions, shown generally in equation (2), are well known in the literature and are discussed in textbooks, such as that by R. T. Morrison and R. N. Boyd entitled "Organic Chemistry," Third Edition, Chapters 12, 19, and 30, Allyn and Bacon, Inc., 1973.

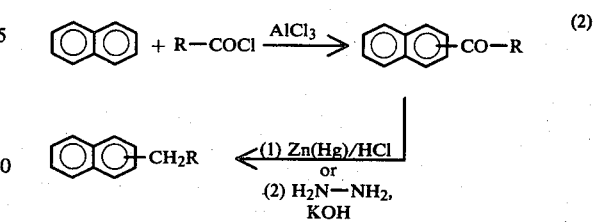

where R = linear alkyl

Sulfonation of the monoalkylnaphthalenes and dialkylnaphthalenes to the sulfonic acid precursors of the sulfonated salts having structures (A)–(D) can be effected with such reagents as concentrated sulfuric acid, oleum, chlorosulfonic acid and liquid sulfur trioxide. The sulfonations are generally effected in inert solvents, such as methylene chloride, chloroform, and 1,2-dichloroethane; at temperatures of 40° C. or below.

Common conditions for sulfonation of naphthalene and various alkylnaphthalenes can also be found in the review by C. M. Suter, "Organic Reactions", Volume 3, Chapter 4, Johy Wiley & Sons, Inc., 1946. For synthesis of the desired monosulfonated and disulfonated alkylnaphthalenes of this invention, careful control of the stoichiometry of the sulfonation reaction is necessary. Despite the various precautions taken, it is often impossible to avoid formation of mixed sulfonated products. Isolation and purification of the desired mono- or disulfonated alkylnaphthalenes is generally effected by fractional crystallization, fractional solubilization, or column chromatography on silica gel, techniques which are preferably done on the salt forms of the sulfonic acid derivative.

The position of substitution of the sulfonate groups on the aromatic rings of the alkylnaphthalene compounds is generally not known with certainty and, in any event, is not considered important in the practice of this invention. However, structure characterization, determination of the number of sulfonic acid groups introduced, and purity of the sulfonate salt derivatives or their sulfonic acid precursors can be determined by a number of known methods: (1) NMR and IR spectroscopic analysis, (2) acidimetric assays (on the sulfonic acid derivatives), (3) metal salt analysis via atomic absorption, and (4) elemental analysis for carbon, hydrogen and sulfur.

The alkali metal salts of the sulfonated alkylnaphthalenes are conveniently prepared by neutralization of a water or alcohol solution of the sulfonic acid derivative with alkali metal hydroxide solutions to the potentiometric endpoint. The salts are recovered by filtration, solvent stripping, or freeze drying, depending on the type of solvent used and whether the salt precipitates directly from the solvent medium. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or are isolated by solvent stripping.

Multivalent metal salts, such as the calcium, magnesium, zinc, and aluminum salts, of the sulfonated products are prepared by methods similar to those described above. In an alternate procedure, multivalent metal salts can be prepared by an ion-exchange reaction between the multivalent ion and either the free sulfonic acid or an alkali metal sulfonate derivative. Ammonium salts of the sulfonic acid derivatives can be prepared by direct addition of ammonia or a primary, secondary, or tertiary organic amine.

The hydrophilic alkylnaphthalene sulfonates of this invention are highly effective in reducing the deposition of plaque during in vitro testing when a suitable balance of hydrophobic and hydrophilic properties is provided in accordance with the foregoing definitions for structures (A) through (D).

Examples illustrating the effect of the hydrophobic/hydrophilic balance on the plaque barrier properties of the alkylnaphthalene sulfonates are found in Tables 1 and 2, in which are summarized the results of tests carried out in accordance with the procedure described below.

The in vitro test procedure employed for obtaining the data reported in Tables 1 and 2 begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or another vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects. Plaque reduction of about 40% or more is considered significant in this test.

TABLE 1

Plaque Barrier Properties of Monoalkylnaphthalene Monosulfonates and Disulfonates Structures:

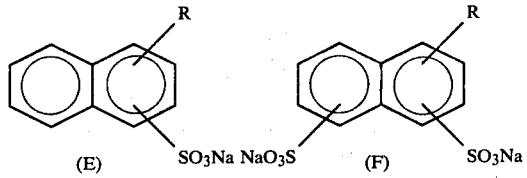

| Naphthalene Derivative | Structure | R | % Plaque Retardation |
| --- | --- | --- | --- |
| Sodium 1-naphthalene sulfonate (control) | E | H | Inactive |
| Disodium 2,6-naphthalene disulfonate (control) | F | H | Inactive |
| Butylnaphthalene | E | $C_4H_9$ | 68 |
| Hexylnaphthalene | E | $C_6H_{13}$ | 68 |
| Hexylnaphthalene | F | $C_6H_{13}$ | Inactive |
| Nonylnaphthalene | E | $C_9H_{19}$ | 65 |
| Dodecylnaphthalene | E | $C_{12}H_{25}$ | 87 |

TABLE 2

Plaque Barrier Properties of Dialkylnaphthalene Sulfonates

Structures:

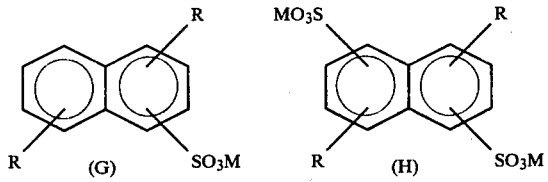

| Naphthalene Derivative | Structure | R | M | % Plaque Retardation |
| --- | --- | --- | --- | --- |
| 2,6-dimethylnaphthalene | G | $CH_3$ | Na | Inactive |
| 2,6-dimethylnaphthalene | H | $CH_3$ | Na | 17 |
| Dibutylnaphthalene | G | $C_4H_9$ | Na | 73 |
| Dihexylnaphthalene | G | $C_6H_{13}$ | Na | 77 |
| Dinonylnaphthalene | G | $C_9H_{19}$ | Na | 76 |
| Dinonylnaphthalene | G | $C_9H_{19}$ | Zn | 76 |
| Didodecylnaphthalene | G | $C_{12}H_{25}$ | Na | 89 |
| Didodecylnaphthalene | G | $C_{12}H_{25}$ | Zn | 74 |
| Didodecylnaphthalene | H | $C_{12}H_{25}$ | Na | 78 |

EXAMPLE 1

Sodium Nonylnaphthalene Monosulfonate

To a stirred solution of 25.4 g (0.100 mole) nonylnaphthalene (King Industries) in 254 ml. methylene chloride was added, over one hour at 21°–27° C., a solution of the sulfonation agent. The latter was prepared by addition of 16.0 g (0.200 mole) liquid sulfur trioxide to a cooled solution of 9.1 g (0.05 mole) triethyl phosphate in 132 ml. methylene chloride. After the addition, the clear, amber solution was stirred at 23°–27° C. for another 34 minutes and 10 ml. ether add to terminate the sulfonation reaction. The solution was solvent stripped and the residual syrup dissolved in 250 ml. ether and the solution extracted several times with 50 ml. portions of water. The combined extracts were neutralized from pH 1.7 to pH 8.4 with 50% sodium hydroxide and the solution air dried at 80° C. to a syrupy residue which was taken up in methanol several times and distilled in vacuo each time to remove methanol and residue water. The residue was slurried in hot methanol, cooled to room temperature, filtered from 0.5 g sodium sulfate solids, and the filtrate stripped free of solvent to give 26.0 g of crude sodium nonylnaphthalene sulfonate contaminated with some triethyl phosphate.

The sodium sulfonate salt was purified by column chromatography on silica gel, grade 950. Elution with toluene gave 10.0 g of pale yellow solids of purified salt. The NMR spectrum indicated an average D.S. (degree of sulfonation) of 1.0 sulfonate groups per naphthalene ring and that random sulfonation on the naphthalene ring had occurred.

EXAMPLE 2

Sodium Didodecylnaphthalene Monosulfonate 10.0 g of Synex ™ DD052, a 50% solution of didodecylnaphthalene sulfonic acid in Norpar 12 solvent, in 20 ml. methanol was neutralized with 8.4 ml. 1.096 N methanolic sodium hydroxide and distilled at 50°–60° C. and at high vacuum to remove solvents. The residual sodium sulfonate salt was an amber, glassy solid, which was soluble in most organic solvents.

EXAMPLE 3

Sodium Dodecylnaphthalene Monosulfonate and Disodium Dodecylnaphthalene Disulfonate A solution of 2.0 g (0.025 mole) liquid sulfur trioxide in 16 ml. methylene chloride was added over 15 minutes at 23°–28° C. to a stirred solution of 5.9 g (0.020 mole) dodecylnaphthalene (King Industries) in 59 ml. methylene chloride. After stirring at 24°–28° C. for another hour, the reaction mixture was solvent stripped in vacuo to a dark brown syrup which was dissolved in methanol and neutralized with 1 N methanolic sodium hydroxide. The neutralized solution was concentrated to gummy orange solids which were dissolved in ethanol, filtered to remove 1.0 g of sodium sulfate, and the filtrate solvent stripped to give 7.2 g of the crude sodium sulfonate derivative.

The crude solids (5.8 g) were purified by column chromatography of a chloroform solution on 58 g. silica gel, grade 950. Gradient elution with 9:1 to 1:1 chloroform methanol blends gave 4.4 g of purified sodium dodecylnaphthalene monosulfonate (D.S. 0.9 via NMR) and 0.5 g of purified disodium dodecylnaphthalene disulfonate (D.S. 1.6 via NMR).

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidal magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A

Mouthwash Solution

| Barrier Agent | 0.5–2.0 % w/w |
|---|---|
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B

Mouthwash Solution

| Plaque Barrier Agent | 0.5–3.0 % w/w |
|---|---|
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C

Abrasive Dentrifice Gel

| Plaque Barrier Agent | 2.0–10.0 % w/w |
|---|---|
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D

Chewing Gum

| Plaque Barrier Agent | 1.0–11.0 % w/w |
|---|---|
| Gum Base | 21.3 |
| Sugar | 48.5–58.5 |
| Corn Syrup (Baume 45) | 18.2 |
| Flavors | 1.0 |
| | 100.0 |

EXAMPLE E

Nonabrasive Gel Dentifrice

| Plaque Barrier Agent | 0.05–30.0 % w/w |
|---|---|
| Sorbistat (preservative) | 0.15 |
| Deionized Water | q.s. |

| -continued | |
|---|---|
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w |
|---|---|
| Distilled Water | q.s. |
| Sodium Saccharin (sweetener) | 0.20 |
| Sodium Benzoate (preservative) | 0.30 |
| FD&C Blue #1 (0.1% aq. soln.) | 0.27 |
| D&C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| Plaque Barrier Agent | 5.00 (dry basis) |
| Flavor | 0.80 |
| | 100.0 |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

I claim:

1. An oral hygiene composition selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays consisting essentially of a therapeutically effective amount for preventing deposition of dental plaque on teeth of a salt of an alkylnaphthalene sulfonate selected from the group consisting of the monoalkylnaphthalene monosulfonate salts of structure (A),

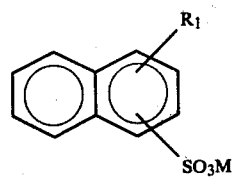
(A)

dialkylnaphthalene monosulfonate salts of structure (B),

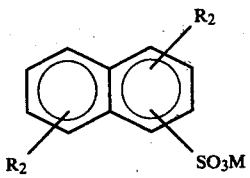
(B)

monoalkylnaphthalene disulfonate salts of structure (C),

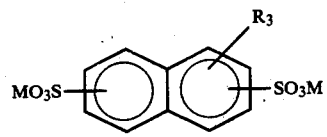
(C)

and dialkylnaphthalene disulfonate salts of structure (D),

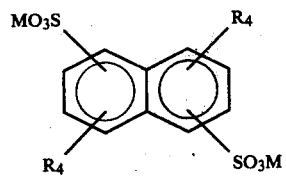
(D)

wherein $R_1$ is a linear or branched alkyl having 4 to 20 carbon atoms, $R_2$ is a linear or branched alkyl having 4 to 12 carbon atoms, $R_3$ is a linear or branched alkyl having 16 to 20 carbon atoms, $R_4$ is a linear or branched alkyl having 8 to 20 carbon atoms, and M is selected from the group consisting of lithium, sodium, potassium, calcium, magnesium, zinc, aluminum, ammonium and the substituted ammonium ions derived from pharmaceutically acceptable organic amines in a pharmaceutically acceptable oral hygiene vehicle compatible with said alkylnaphthalene sulfonate salt.

2. A method of preventing deposition of dental plaque on teeth comprising periodically applying to the teeth a composition of claim 1.

3. The method of claim 2 wherein said composition is applied from about 1 to about 3 times per day.

* * * * *